United States Patent
Luo

(10) Patent No.: US 11,666,485 B2
(45) Date of Patent: Jun. 6, 2023

(54) ADJUSTABLE MASK

(71) Applicant: LumosTech, Inc., San Francisco, CA (US)

(72) Inventor: Biquan Luo, San Francisco, CA (US)

(73) Assignee: LumosTech, Inc., San Francisco, CA (US)

(*) Notice: Subject to any disclaimer, the term of this patent is extended or adjusted under 35 U.S.C. 154(b) by 421 days.

(21) Appl. No.: 16/803,961

(22) Filed: Feb. 27, 2020

(65) Prior Publication Data

US 2020/0276053 A1    Sep. 3, 2020

Related U.S. Application Data

(60) Provisional application No. 62/835,473, filed on Apr. 17, 2019, provisional application No. 62/814,257, filed on Mar. 5, 2019, provisional application No. 62/812,683, filed on Mar. 1, 2019.

(51) Int. Cl.
| | |
|---|---|
| *A61F 9/04* | (2006.01) |
| *A61M 21/02* | (2006.01) |
| *A61N 5/06* | (2006.01) |
| *A61M 21/00* | (2006.01) |

(52) U.S. Cl.
CPC .............. *A61F 9/04* (2013.01); *A61M 21/02* (2013.01); *A61N 5/0618* (2013.01); *A61M 2021/0044* (2013.01); *A61N 2005/063* (2013.01); *A61N 2005/0648* (2013.01)

(58) Field of Classification Search
CPC ...... A61F 9/04; A61M 21/02; A61M 2021/0044; A61M 2205/3592; A61M 2205/3606; A61M 2205/50; A61M 2205/505; A61M 2205/8206; A61M 2209/088; A61M 2210/0612; A61N 5/0618; A61N 2005/063; A61N 2005/0648; A61N 5/06–2005/073

See application file for complete search history.

(56) References Cited

U.S. PATENT DOCUMENTS

| | | | | |
|---|---|---|---|---|
| 4,502,476 A | * | 3/1985 | Welt | A61F 9/04 |
| | | | | 128/858 |
| 7,268,669 B2 | * | 9/2007 | McEvoy | A61F 11/14 |
| | | | | 381/372 |

(Continued)

OTHER PUBLICATIONS

Hoshaw, A New Way to Avoid Jet Lag:Sleep With Flashing Lights, KQED, Published Feb. 12, 2016, https://www.kqed.org/futureofyou/110216/a-new-way-to-avoid-jet-lag-sleep-with-flashing-lights (Year: 2016).*

(Continued)

*Primary Examiner* — Jonathan T Kuo
(74) *Attorney, Agent, or Firm* — Scale LLP

(57) ABSTRACT

In an embodiment, a sleep mask is provided, which may include a site (such as a pocket near the center of the forehead), for holding electronical components for implementing a circadian rhythm disorder treatment program. Optionally, the sleep mask may also include one or more holes for locating and securing light pipes that are connected to lights for producing lighting that adjust a user's circadian pattern based on the circadian rhythm disorder treatment program. Optionally, the sleep mask also includes adjustable straps.

21 Claims, 15 Drawing Sheets

(56) References Cited

U.S. PATENT DOCUMENTS

| | | | | |
|---|---|---|---|---|
| 8,852,073 | B2* | 10/2014 | Genereux | A61M 21/02 600/25 |
| 10,888,709 | B2* | 1/2021 | Hill | A61N 5/0622 |
| 2006/0097880 | A1* | 5/2006 | McEvoy | A61F 11/14 340/573.1 |
| 2013/0060306 | A1* | 3/2013 | Colbauch | A61N 5/0618 607/88 |
| 2013/0184516 | A1* | 7/2013 | Genereux | A61M 21/02 600/28 |
| 2016/0193442 | A1* | 7/2016 | Adamczyk | A61M 21/02 600/27 |
| 2016/0220841 | A1* | 8/2016 | Hill | A61N 5/0622 |

OTHER PUBLICATIONS

LumosTech, Reserve your LumosTech Smart Sleep Mask, Published/captured Apr. 21, 2017, https://web.archive.org/web/20170421084937/http://lumos.tech:80/reserve/ (Year: 2017).*

* cited by examiner

ADJUSTABLE MASK

RELATED APPLICATIONS

This application claims priority benefit to

U.S. provisional Application Ser. No. 62/812,683, entitled "ADJUSTABLE MASK," filed Mar. 1, 2019, by Biquan Luo;

U.S. provisional Application Ser. No. 62/814,257, entitled "Circadian Rhythm Adjustment System," filed Mar. 5, 2019, by Biquan Luo; and U.S. provisional Application Ser. No. 62/835,473, entitled "Circadian Rhythm Adjustment System," filed Apr. 17, 2019, by Biquan Luo.

All of the above Applications are incorporated herein by reference.

FIELD OF THE INVENTION

This invention relates to the field of comfortable and effective designs of sleep masks

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Eye masks for sleep have different functional and aesthetic designs depending the usage of the mask.

SUMMARY OF THE INVENTION

An embodiment includes a sleep mask design that holds the electronics and delivers the light through the light pipes and holes. Also in an embodiment, a sleep mask strap includes a tunnel structure that allows adjustment based on head size, ear position and size. The sleep mask may include a housing for electronics that may be comprised of two major foam structures having a sandwich shape. In between the sandwich is a pocket and the pocket may be located in the mask at or around the forehead area, where the electronics may be housed. The electronics are housed in an enclosure that is, in one embodiment, made of plastic to protect the electronics from damage by external forces. The pocket may open from the top of the mask so the electronics can be removed and reinsert as needed. The electronics may be registered (e.g., located and secured accurately) to the mask through a button-like mechanical lock design, and the pocket may be sealed with hook and loop or other mechanism to keep the electronics in place. In one embodiment, the electronic component may be permanently sealed into the fabric. Electronic component is sealed and contains no connectors, holes or openings such that it achieves maximum ingress protection. Communication and charging of the internal battery are both achieved wirelessly (e.g. Bluetooth, BLE, WiFi for former, and Qi protocol for latter). The mask can be washed in its integral form without taking out electronics.

In an embodiment, the strap that holds the mask on the wearer's head has elastic bands that attached to pads that includes a hook and loop material (e.g., Velcro®), so that pads may be easily attached to, and separated from, one another. One or two elastic bands (or straps) may be attached to each side of the mask at one end of the elastic bands and a pad may attached to the other end of the elastic bands. There may be two pads that attach together, via the hook and loop material to help secure the mask in place while being worn. One of the two pads may be adjustably fixed to bands coming from the left side of the mask and the other of the two pads may be adjustably fixed to one or more bands coming from the right side of the mask. The bands may also be referred to as straps.

Optionally, the eye mask delivers a circadian rhythm disorder treatment program (e.g., light programs) before or during sleep, or when waking up. Optionally, the mask has another purpose other than providing the circadian rhythm therapy or light therapy. Optionally, the eye mask contains electronics that tracks sleep/wake state and/or sleep quality. Optionally, the mask may not have any electronics in the mask.

Optionally, the electronic component has two translucent structures that protrudes from the inner side (that is the side that faces the user's eyes) of the sandwich structure to the surface of the eyehole and delivers the light (light pipes) around the eye area. Optionally, each light may include a diffuser, a scattering material, and/or a diverging lens to spread the light more evenly across the user's eyes. In an alternative embodiment, there may be multiple lights and light pipes. In another embodiment, multiple light pipes can direct the lights from a single light source.

In an embodiment, the electronics may be aligned and registered by the light pipes in their position related to the eye mask. The light pipes are registered at the light pipe holes on the eye mask. In other words, the light pipes are installed in holes in the eye mask through a button-like structure at the end. In an embodiment, the electronics housed in the plastic enclosure is aligned and registered to the mask through a charging port with a button-like structure at the end to keep the electronics in place. In other words, the charging port is accessible through a hole in the eye mask at the top. The electronics may include one or more light sources (e.g., an LED or lightbulb) and hardware (e.g., a processor and memory) for running a program that delivers the light treatment to the user. The electronic turns the light sources on according to the light treatment program, and the light is sent through the light pipe towards the user.

Optionally, the mask has adjustable straps that hold the mask on the user's head. Optionally, the mask may include tunnels or channels in which the strap is located to hold the strap to the mask. The strap may have two parts each connected to a different side of an eye mask (e.g. a sleep mark). Each part of the strap includes a hook and loop material that connect to one another to connect the two parts of the strap to one another. In an embodiment, the width of the loop formed by the straps (when connected to one another) and the mask is determined by where the two straps are connected to one another by the hook and loop material. The hook and loop material may be located on pads that have tunnels or channels through which the strap is threaded to hold the pads to the strap. In an embodiment, since the mask attaches to the user's head by a flexible strap, and since the size of the loop formed by the strap may be adjusted (e.g., by placing connecting the hook and loop material of the two halves of the strap together in different locations), the mask may be adjusted to any head size and position of the user's ears.

In an embodiment, the strap from each side of the mask forms a loop that goes through the tunnel or channel of one pad. One part of the loop spans above the user's ear, and another part spans under the user's ear, with the third part going through the tunnel or channel of the pad.

Any of the above embodiments may be used alone or together with one another in any combination. Inventions encompassed within this specification may also include embodiments that are only partially mentioned or alluded to or are not mentioned or alluded to at all in this brief summary or in the abstract.

BRIEF DESCRIPTION

In the following drawings like reference numbers are used to refer to like elements. Although the following figures depict various examples of the invention, the invention is not limited to the examples depicted in the figures.

Figure 1A:
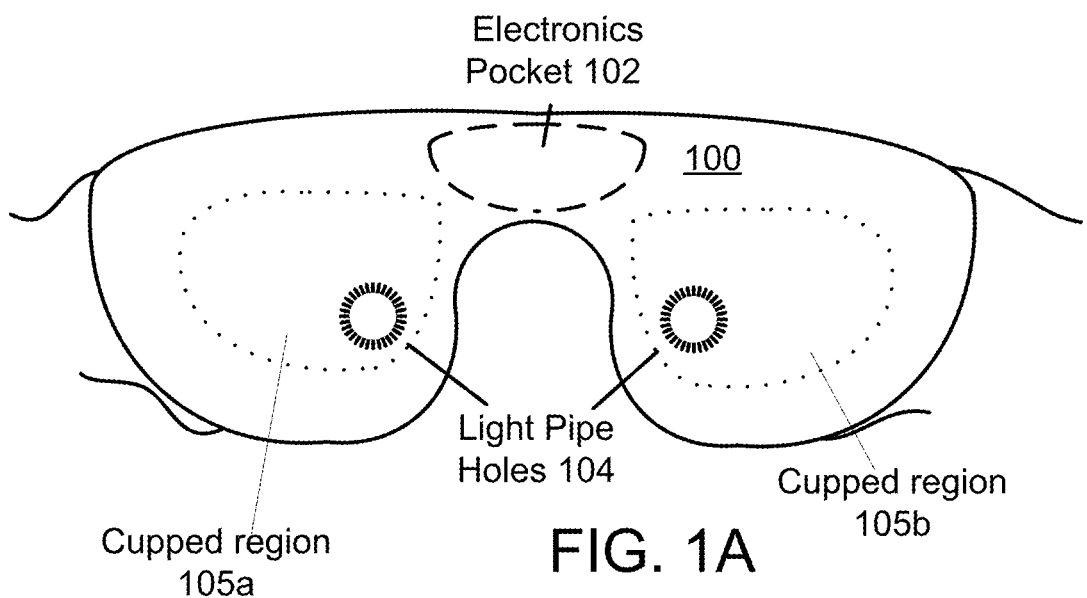
FIG. 1A shows a diagram of an embodiment of the mask prior to placing the hardware into the mask.
Figure 1B:
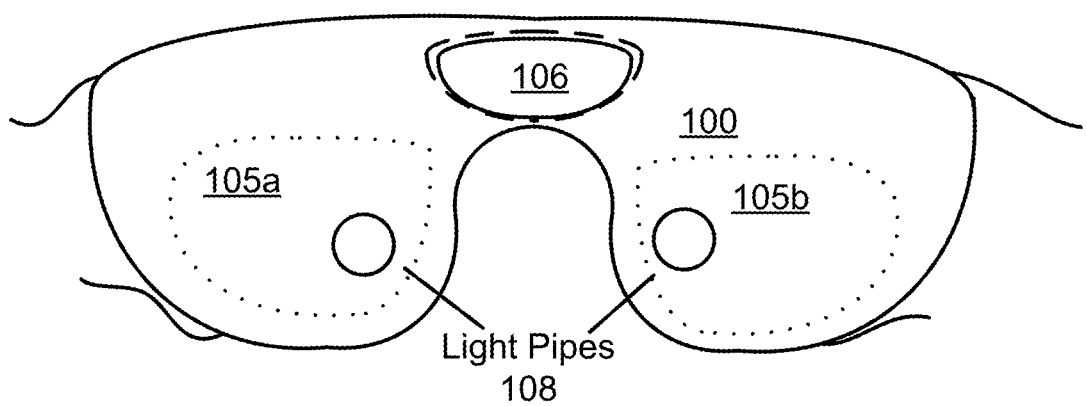
FIG. 1B shows a diagram of an embodiment of the mask of FIG. 1A after the hardware has been installed.
Figure 1C:
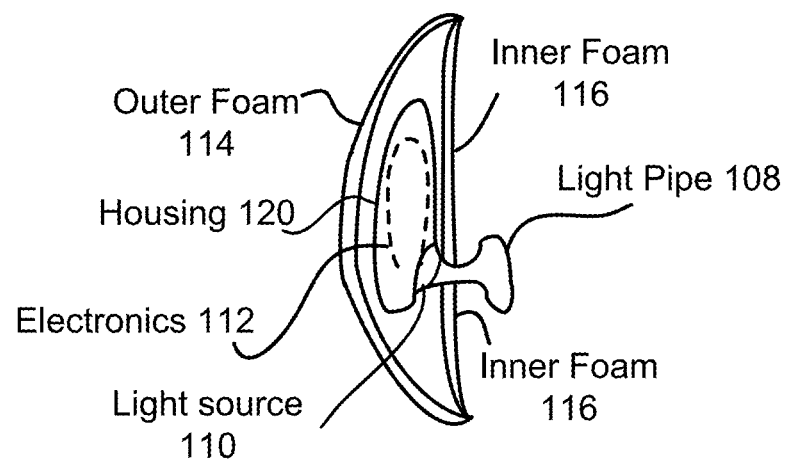
FIG. 1C shows an embodiment of a cross section of the mask with the electronic insert inside the pocket and one light pipe for delivering the light generated to the user.
Figure 1D:
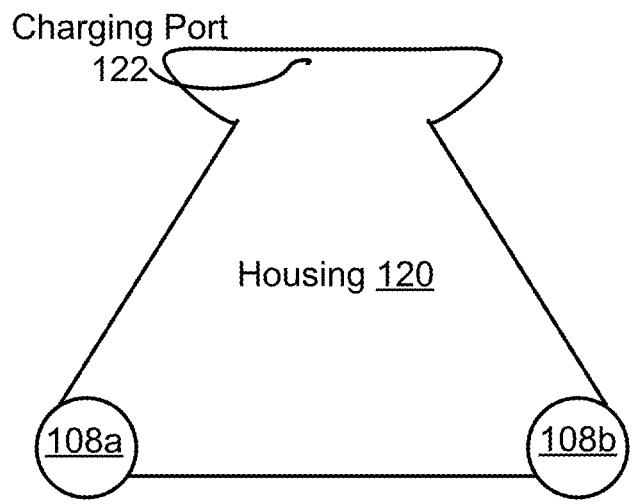
FIG. 1D shows a front view of the embodiment of an electronic insert.
Figure 1E:
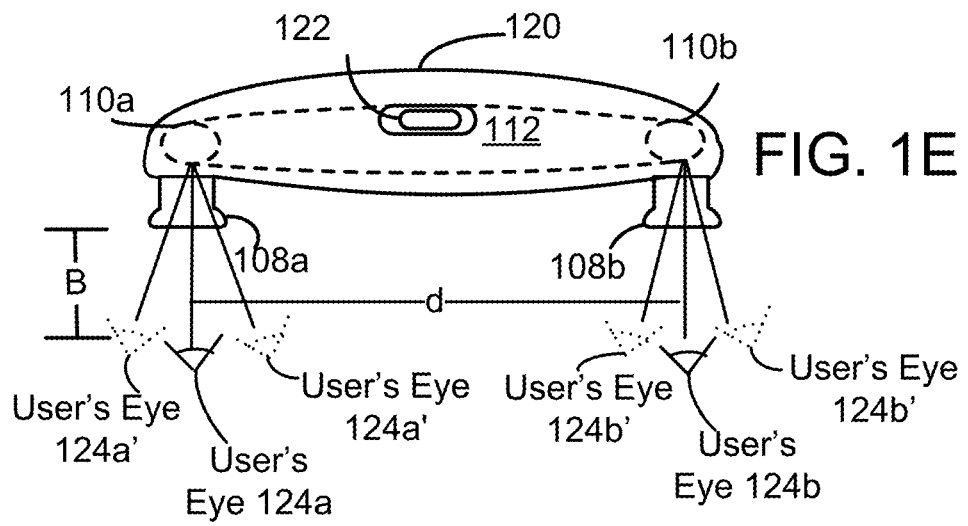

FIG. 1E should a top view of the embodiment of the electronic insert of FIG. 1D.

Figure 1F:
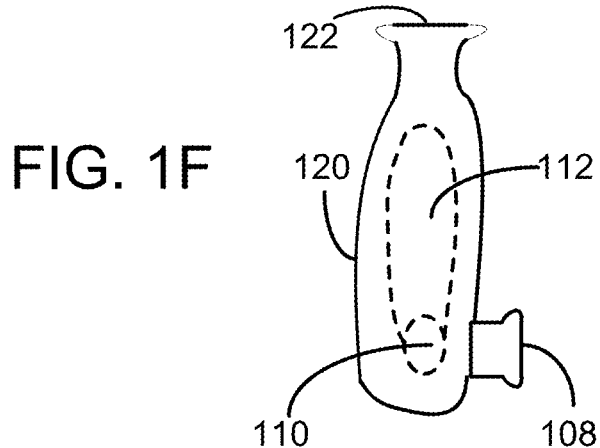

FIG. 1F shows a side view of the embodiment of the electronic insert of FIG. 1D.

Figure 1G:
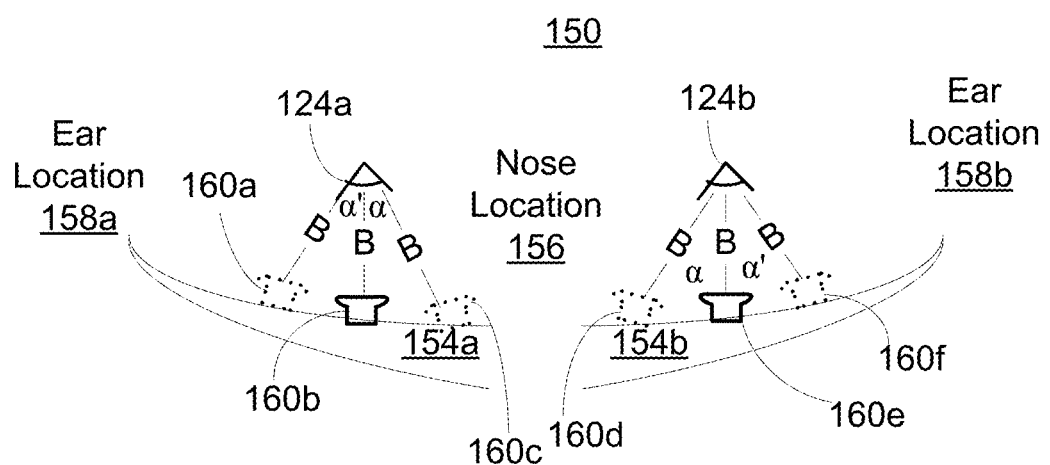

FIG. 1G shows the angle and dimension design of the electronic insert of FIG. 1D.

Figure 2:
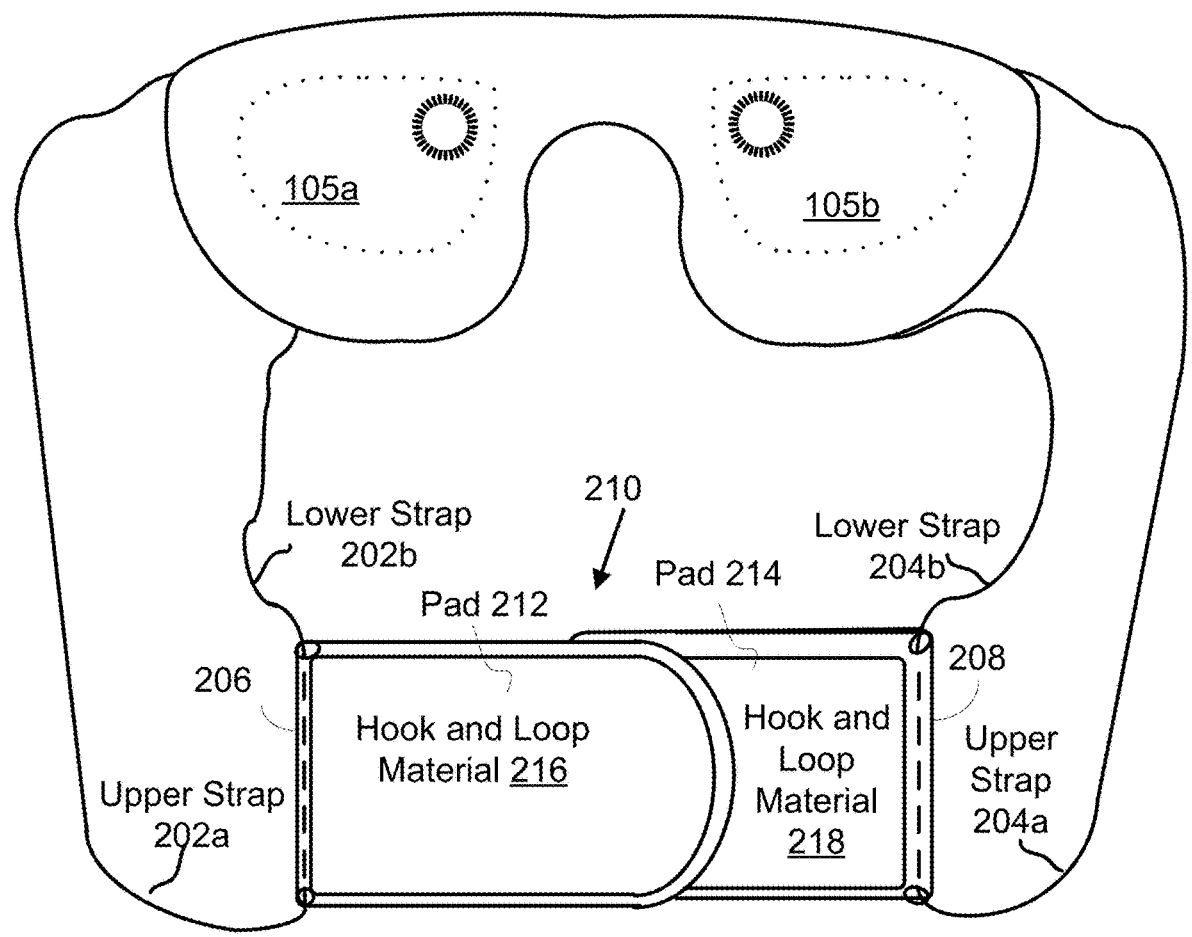

FIG. 2 shows a diagram of an embodiment of a mask illustrating the strap.

Figure 3:
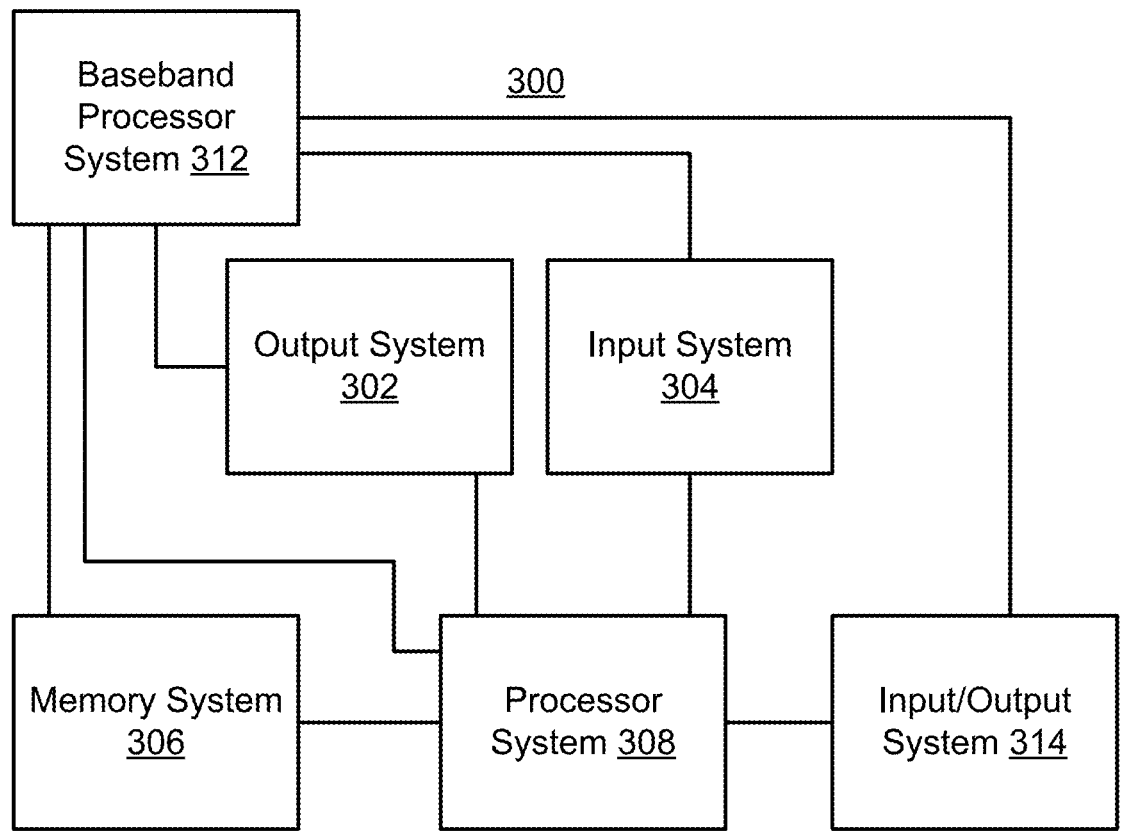

FIG. 3 shows a block diagram of an embodiment of a mobile device/computing device used in the system of FIG. 1.

FIGS. 4-11 are diagrams of an embodiment of the mask.

Figure 4:
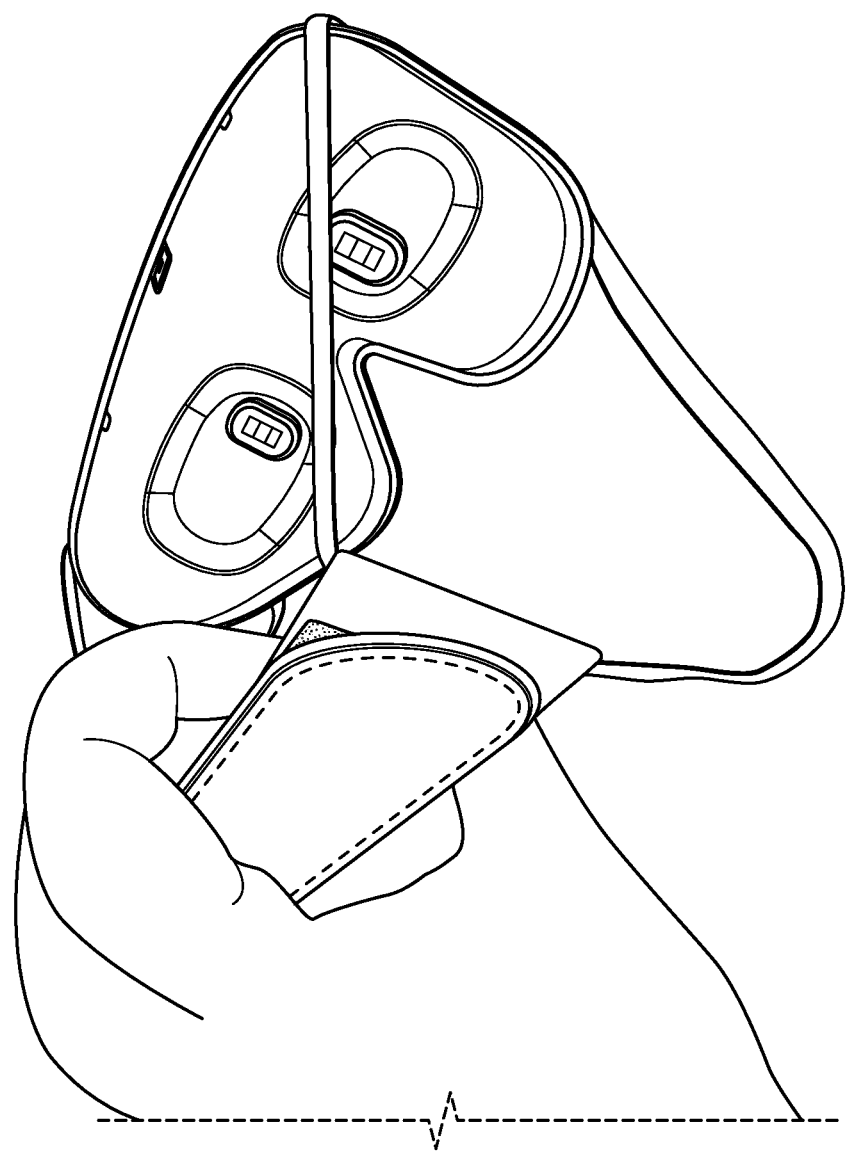
Figure 5:
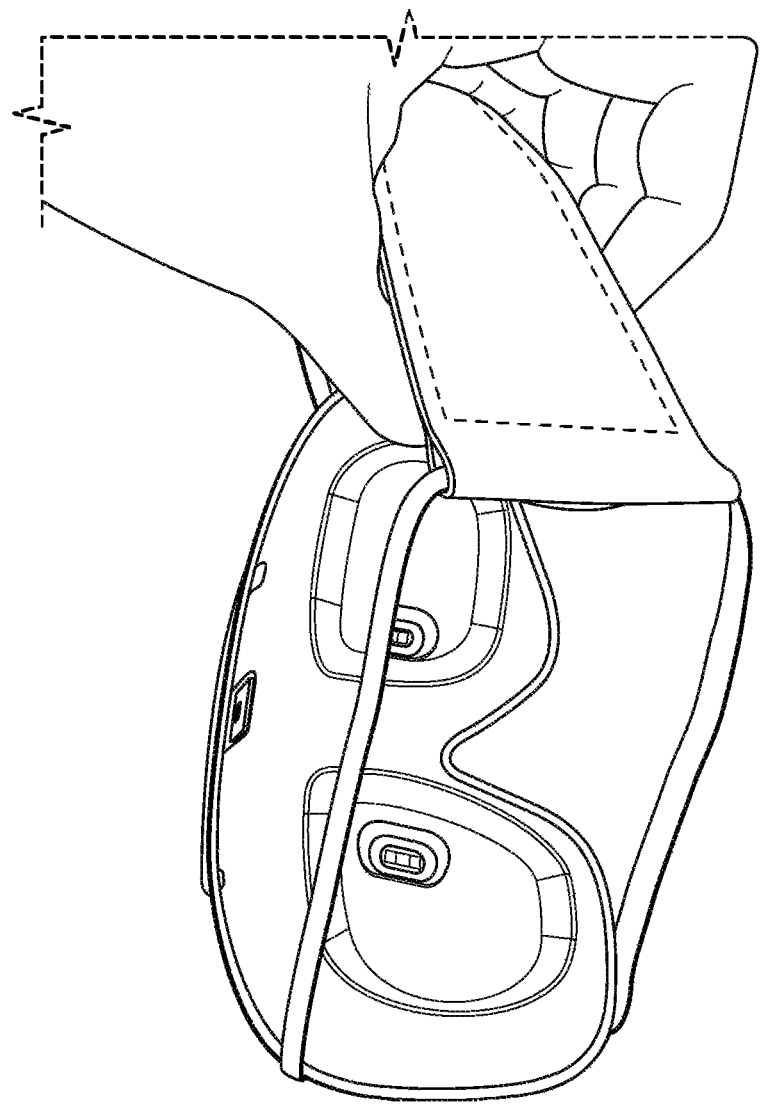

FIGS. 4 and 5 are diagrams showing the mask and straps.

Figure 6:
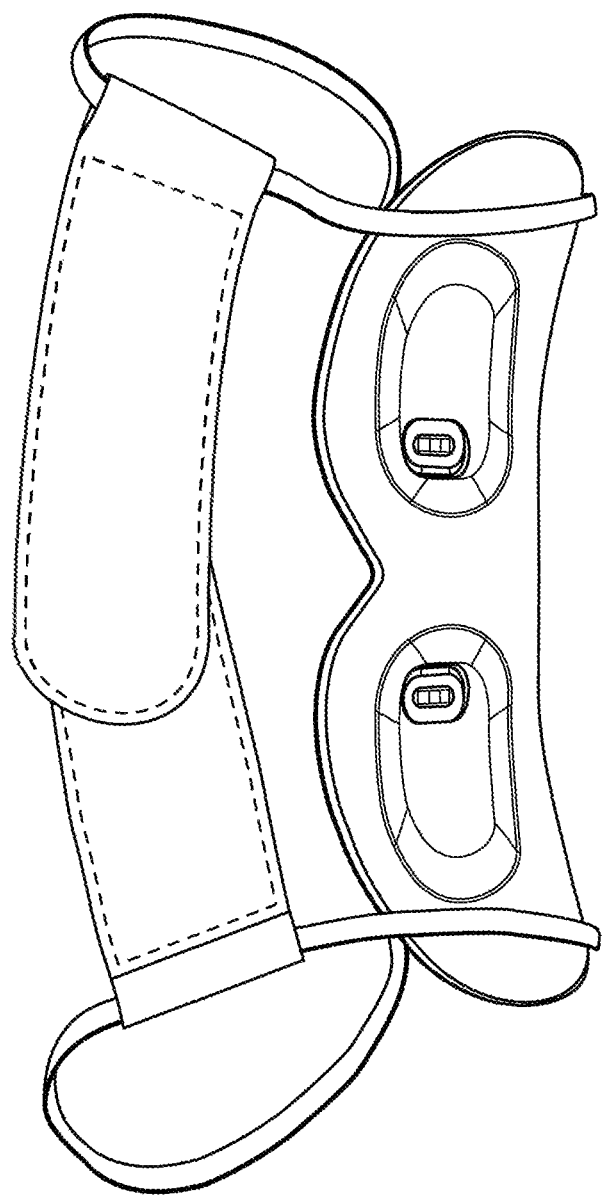

FIG. 6 shows another a diagram of the mask and straps in which the hook and look materials is visible on one of the pads of the fastener that fastens the mask to the head.

Figure 7:
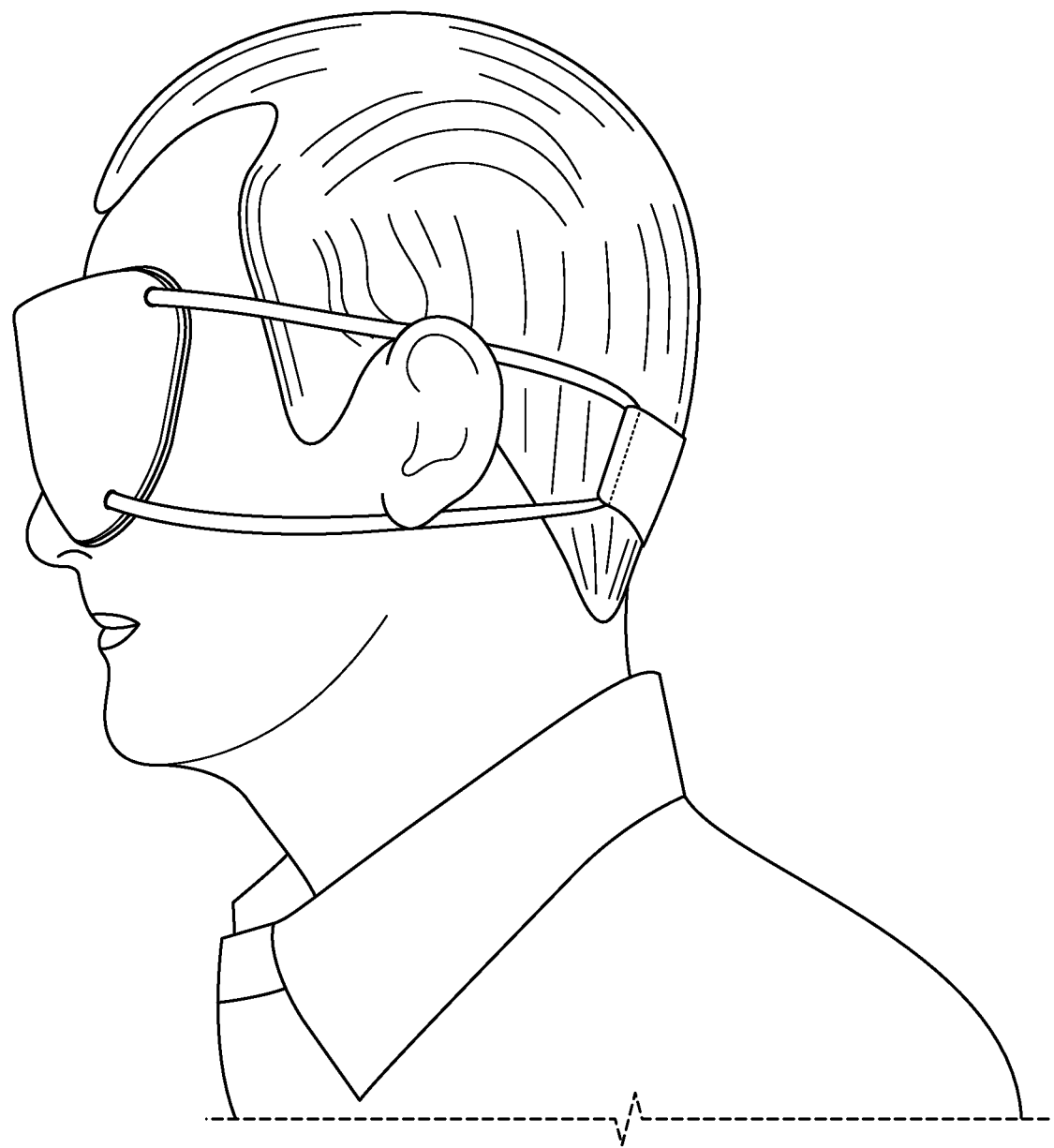

FIG. 7 shows a user wearing an embodiment of the mask.

Figure 8:
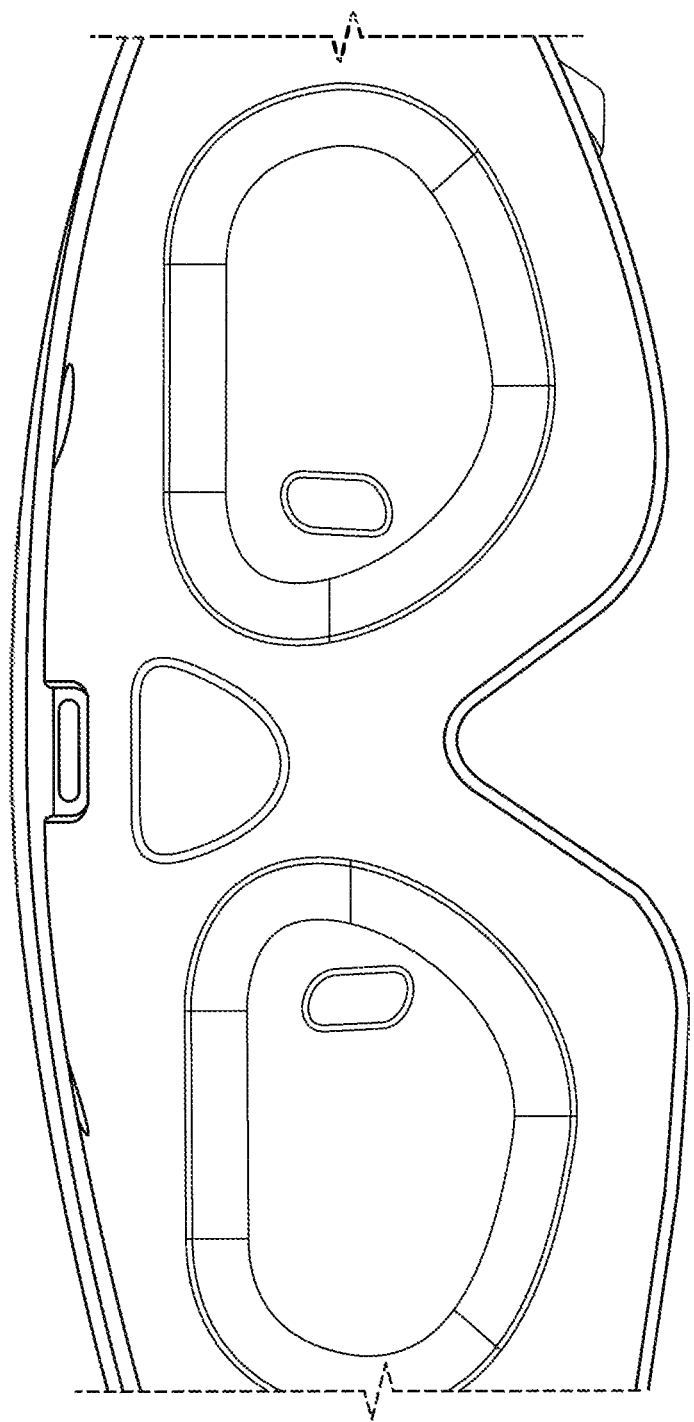

FIG. 8 shows a better view of the cups, without the light pipes in place, on the mask that cover the eyes of the user.

Figure 9:
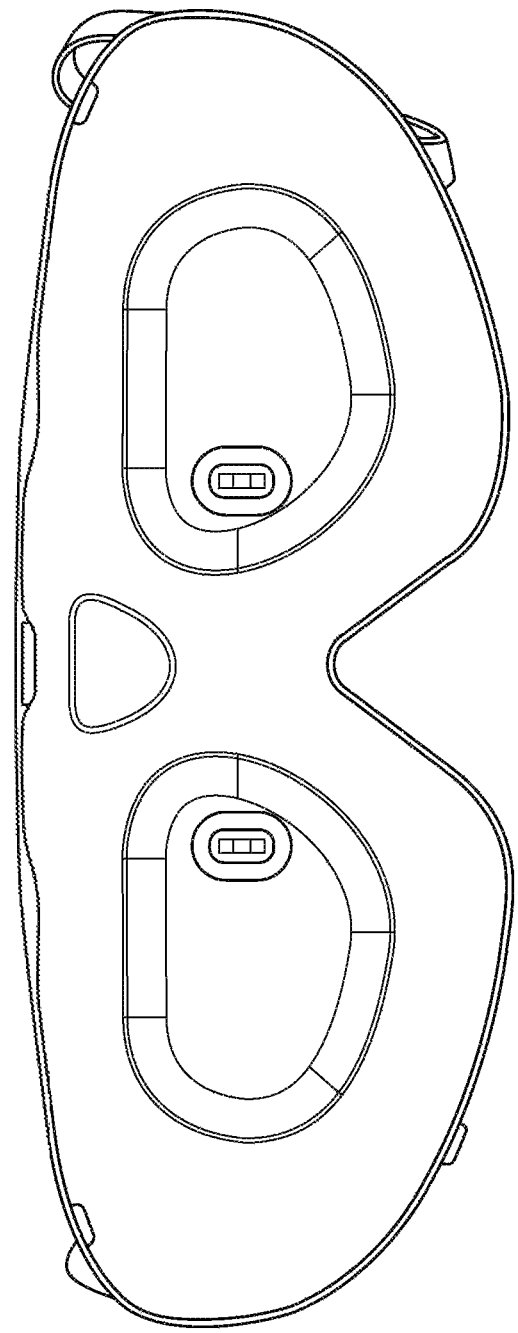

FIG. 9 shows another view of the cups on the mask in that cover the eyes of the user, but with the light pipes installed.

Figure 10:
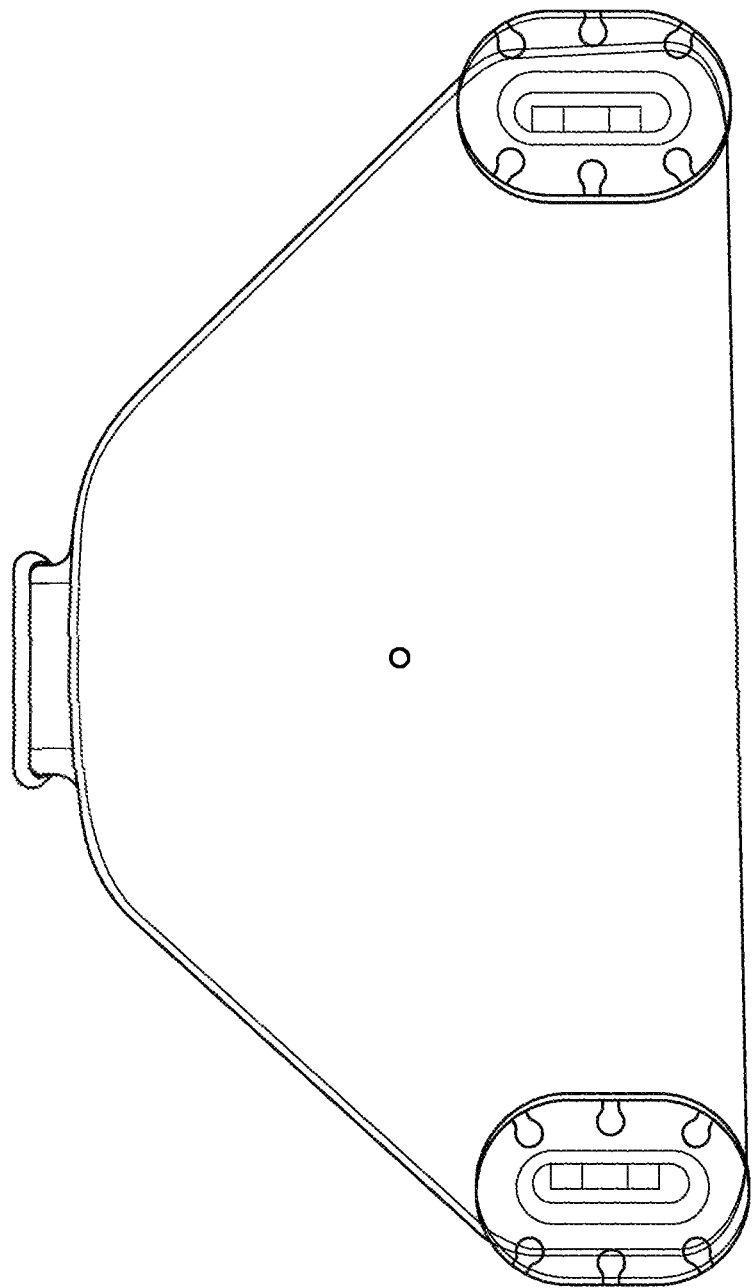

FIG. 10 shows an electronics module that fits into the mask.

Figure 11:
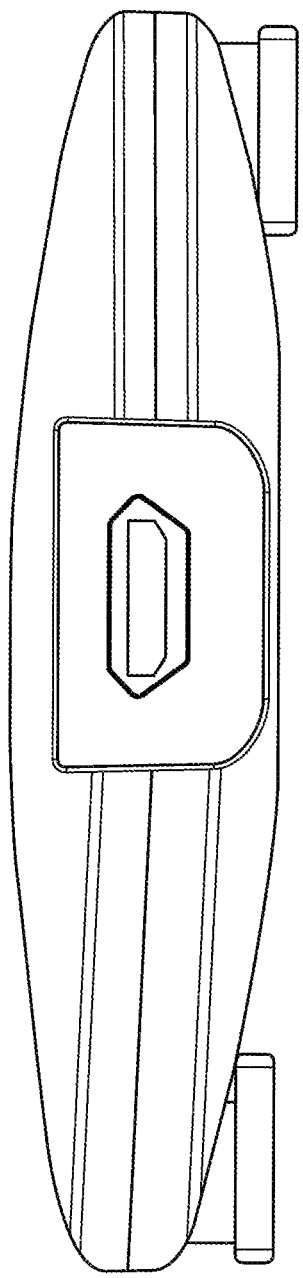

FIG. 11 shows a top view of the electronics module, which fits into the mask.

Figure 12:
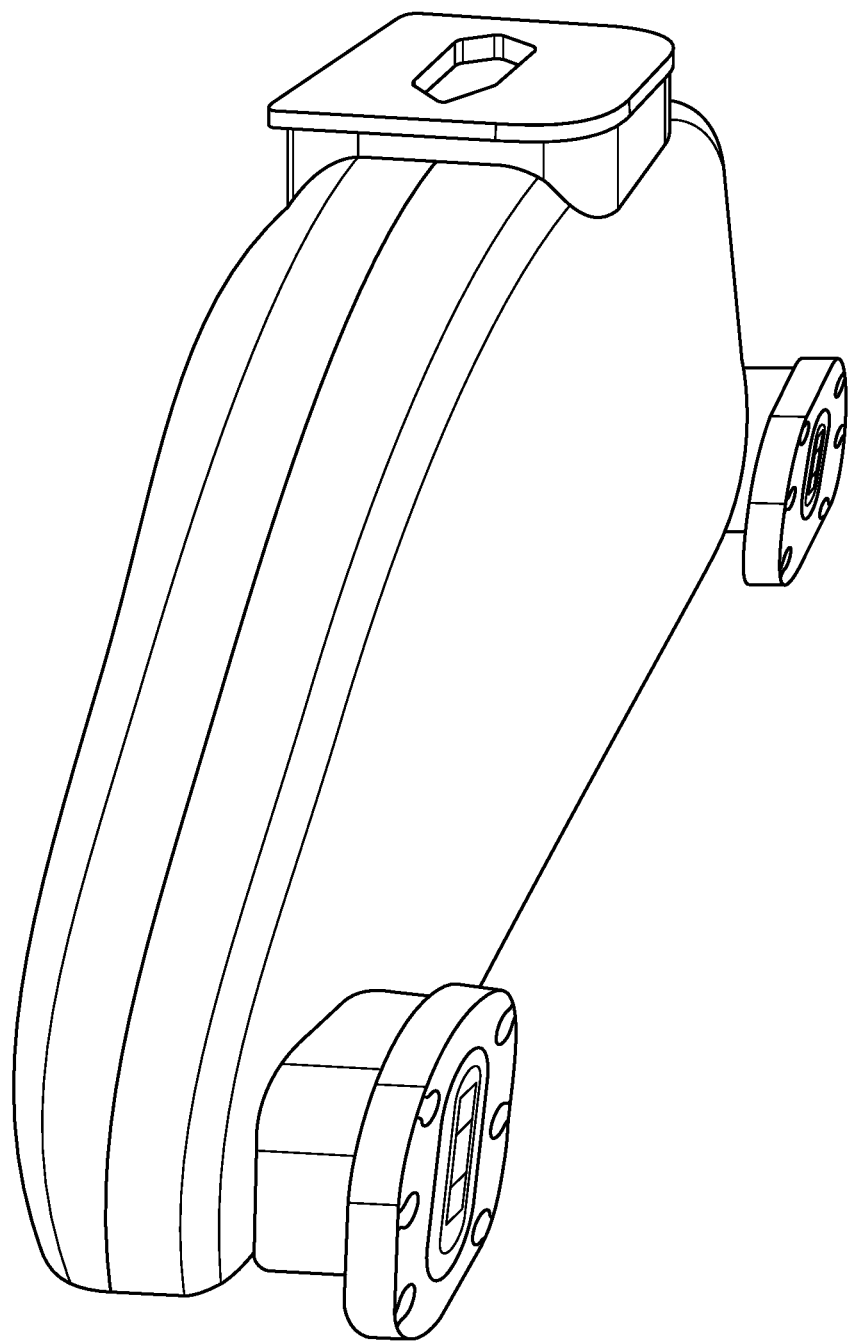

FIG. 12 shows a perspective view of the electronics module, with details about the light pipes.

DETAILED DESCRIPTION

Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

The disclosures of the devices and methods of this application and the appendix describe different parts of what can be the same devices, methods, and/or systems. Any element of this disclosure may be used in the embodiments of the appendix and any element of appendix may be used in the embodiments of this application.

For a smart sleep mask that contains electronic components, it may be desirable to design the mask so that the mask not only has the ability to hold the electronics and to deliver the circadian rhythm disorder treatment program (e.g., a light program), but also the mask should remain in its position on the user's head while in use, as well as being worn in bed comfortably in all, nearly all, or a large variety of sleeping positions. The fabric and foam components are generally comfortable in a large variety of configurations. However, when incorporating rigid electronics components in the mask it is more difficult to ensure comfort. In various embodiments of this specification (but not all embodiments), the system of the mask may be built so as to meet a balance of six features (in addition to other criteria: 1) the mask should is soft enough not to apply an uncomfortable pressure against the user's face when sleeping on the side or face-down; 2) the mask provides enough cushion around the rigid electronics to protect the electronics from environmental damage and to protect the face from pressure from the electronics; 3) while providing enough cushion with soft materials, the mask still breathes (e.g., to help ensure that the electronics cools properly and does not over heat); 4) the eye regions of the mask is be recessed enough and away from the eyes to prevent rubbing against the user's eyes; 5) the mask effectively blocks environmental light; 6) the mask is adjustable to different head sizes and shapes. In addition to or as an alternative to cooling the electronics by ensuring that the mask breathes (and therefore is cooled by air), a heat sink may be included to help cool the electronics. For example, one or more wires and/or pieces of heat conductive material (e.g., metallic materials) may be placed, so that one end of the heat conductive material is in contact with on in the vicinity of the electronic circuit board or substrate (while being electrically insulated from the electronic components), and another end of the heat conductive material may be in contact with air.

FIG. 1A shows a diagram of an embodiment of the mask 100 with empty electronics pocket 102 and light pipe holes 104, prior to placing the hardware into the electronics pocket 102 and the light pipes into light pipe holes 104 of the mask 100. FIG. 1B shows a diagram of an embodiment of the mask of FIG. 1A after the hardware, electronics 106 and light pipes 108 have been installed. FIG. 1C shows that light pipe 108 may be connected to an LED (or other light source 110) and/or other electronics 112 on one side of the mask and light pipe for delivering the light generated to the user. The light pipe 108 has an enlarged part at the end in the shape of a button that goes through the light pipe hole on the inner side of the eye mask to hold the electronics and the mask together tightly in the right place. Electronics 106, light pipes 108, light source 110 and/or other electronics 112 may be held between outer foam 114 and inner foam 116. In an embodiment, the electronic 106, light pipes 108, light source 110 and/or other electronics 112 are on one single rigid Printed Circuit Board (PCB) and held in a single rigid plastic enclosure. In an alternative embodiment, the electronics 106, light pipes 108, light source 110 and/or other electronics 112 are on one flexible PCB and the enclosure is a made of a flexible plastic, another material, and/or is made to be flexible or semi-flexible. FIGS. 1C-1F show different views of a housing within in which electronics 106, light sources 110, and/or electronics 112 are enclosed. In an embodiment, the electronics 106 and/or other electronics 112 are on one rigid PCB while the light pipes 108 and light source 110 are held on separate PCBs and connected by wires. In an embodiment, the light source 110 is part of electronics 106 or 112. In an embodiment, electronics 106 or 112 is part of light source 110. In an embodiment, electronics 106 or 112 and light source 110 are separate units and electronics 112 controls light source 110. Optionally, the light pipe 108 and the light source 110 may be connected with one another mechanically, e.g. by glue. Electronics 106 and/or electronics 112 may communicate wirelessly with one another and/or the light source 110. Optionally, the light pipe and light source 110 may be connected directly to the electronics 106. Optionally, the light source 110 may be connected directly to the electronics 106 and optical fibers may carry the light to the light pipes 106 and/or the user from electronics 106. Optionally, the light source 110 may be located on the same PCB, and the light pipes 108 may be made from plastics that are adhered to the PCB board. In other embodiments, a PCB is not used. The mask 100 includes two cupped regions 105a and 105b that have a shape, so as to surround the user's eye sockets, which is indicated by the dotted line that surround the light pipes.

FIGS. 1D-1G show an embodiment of an electronic insert in a plastic case with two light pipes. FIG. 1D shows a front view of housing 120. Housing 120 may protect and hold electronics 106 and/or electronics 112 in place. Housing 120 may be made from a hard resilient plastic and/or may include (e.g., made from) softer materials. Charging port 122 may be used for charging the battery that powers electronics 106 and/or electronics 112. FIG. 1E shows a top view of housing 120, which shows the connector that makes up charging port 122 and FIG. 1F shows another side view of housing 120. In FIGS. 1E and 1F, electronics 112 and light sources 110a and b are shown in dashed lines, because electronics 112 and light sources 110a and b are hidden from view. FIG. 1E shows that the two light pipes are spaced apart by a distance d, and an angle α or α' is made between a line connecting the center of the light pipes and the center of the user's eyes, and line perpendicular to the line connecting the two light pipes, representing the angle between the center of the light pipe and the center of the user's eye pointing from the pupil. The distance d and the angle α and α' are discussed below. In FIG. 1G, shows a configuration 150 of the adjustable mask of FIG. 1. FIG. 1G shows different possible locations of the light pipes 108a and 108b. Mask portions 154a and 154b are portions of mask 100. For clarity, the rest of the mask 100 is not shown. As a reference for the direction of the angles nose location 156 and ear locations 158a and 158b are labeled. Light pipes 160a-c show possible locations for light pipe 108a for different embodiments mask 100. Similarly, light pipes 160d-f show possible locations for light pipe 108b for different embodiments mask 100. Although light pipes 160b and 160g are drawn in solid lines and light pipes 160a, 160c, 160d, and 160f are drawn in dotted lines, each of light pipes 160b and 160g and light pipes 160a-160f represent possible positions of light pipes 108a and 108b. Although there may be more than two light pipes, since only two are needed (one for the left eye and one for the right eye), only two were drawn in solid lines. In FIG. 1G, B is the distance between the surface of the eye and the light pipe, the angle α is the angle of a diagonal line may between the user's eye 124a or 124b and the light pipe (160c and 160d) when the light pipe is between the eye 124a or 124b and the nose location 154, respectively. The angle α' is the angle of a diagonal line may between the user's eye 124a or 124b and the light pipe (160a and 160f) when the light pipe is between the eye 124a or 124b and the ear locations 158a and 158b, respectively.

The Light Pipes

The light pipes direct the lights from the light source to the user's eyes. In one embodiment, the light pipes are connected directly on the PCB over the location of the light sources (e.g. LED) (FIG. 1D-G). The light pipes, and light sources, are separated by a distance d of 30-150 mm apart from each other, and located within a distance B of 5-25 mm away from the surface of the user's eyes. The direction of the light pipes points at an angle α=0-72 degrees from the direction that is perpendicular to the pupil opening of the user's eyes if the light pipes are located closer to the nose than the ears, or at an angle α'=0-86 degrees from the direction that is perpendicular to the pupil opening of the user's eyes if the light pipes are located closer to the ears than the nose (FIG. 1E and FIG. 1G). In one embodiment, α and α' are both 0 degree. In one embodiment, the light pipes may include a diffuser, a scattering material, and/or a diverging lens to spread the light more evenly across the user's eyes. In one embodiment, the light pipes may be clear. In one embodiment, there may be multiple the light pipes within one cupped eye socket, with at least one pointing directly to the pupil of the user's eyes within the angle α and α' and distance B and d described above. In one embodiment, there may be reflective materials inside the eye sockets to redirect the lights coming out of the light pipe into the user's eyes. In an embodiment, the light pipes may be flexible or adjustable to adapt to different facial structures such as pupillary distance.

The Strap

FIG. 2 shows a diagram of an embodiment of a mask illustrating the strap. The strap may be comprised of one strap at each side (e.g., strap 202 having upper strap 202a and lower strap 202b and strap 204 having upper strap 204a and lower strap 204b). The straps 202 and 204 each goes through a tunnel (e.g., tunnels 206 and 208) or slot, forming a double-strap structure that allows the adjustment of the length of the upper segment (upper straps 202a and/or 204a) and lower segment (lower straps 202b and/or 204b). The strap from each side of the mask forms a loop that goes through the tunnel 206 or 208 one pad. One part of the loop (the upper strap 202a and 204a) spans above the user's ear, and another part (the lower strap 202b and 204b) spans under the user's ear, with the third part going through the tunnel the pad (206 or 208). The double strap design enables the mask to be worn with the two straps across the upper and lower rim of the ears, individually, to keep the mask in place on the user's head without stretching on the back of the ears.

The tunnel/loop structure (e.g., tunnels 206 and 208) and the relative movement of the strap through the tunnel/loop allows the adjustment of the upper and lower segment of the strap, so the mask can be adjusted according to different ear sizes, head sizes, and positions.

FIG. 2 shows a diagram of an embodiment of a mask 100 illustrating the strap. For example, the fastener 210 having pads 212 and 214, which may be made from hook and loop material 216 and/or 218, such as Velcro®. In an embodiment, hook and loop material 216 is on both sides of pad 212 and hook and loop material 218 is on both sides of pad 214. In an embodiment, hook and loop material 216 is on at least one side of pad 212 and/or hook and loop material 218 is on at least side of pad 214. Optionally the side of pad 212 that has hook and loop material 216 faces the opposite direction as the sides of pad 214 that has hook and loop material 218, when the straps are not twisted, so that when the straps are not no twisted, the side of pad 212 that has hook and loop material 216 faces the side of pad 214 that has hook and loop material 218. The hook and loop material piece enables the adjustment of the circumference, so the mask 100 can be adjusted to different head sizes. In other embodiments other straps, pads, and/or fasteners may be used.

Comfort

The mask uses light, soft, and breathable fabric and foam materials for outer foam 114 and/or inner foam 116 to ensure the comfort of the mask while still having the ability to house the electronics. The mask may include straps that include fasteners for fastening the straps to one another.

FIG. 3 shows a block diagram of a mobile device/computing device 300 used in and/or with the system of FIG. 1. The device 300 may include output system 302, input system 304, memory system 306, processor system 308, baseband processor system 312, and input/output device 314.

Device 300 is an example of a device that may be used in or with the system of FIG. 1. Device 300 may be a mobile phone, tablet computer, laptop computer, and/or desktop computer that is used to control the electronics that is the mask 100 and/or may be located in the mask 100. In an embodiment, device 300 is an embodiment of electronics 106. In an embodiment, device 300 is a combination electronics 106, a mobile device, and a device located in the cloud (which the user may interact with, via a wide area network, such as the Internet and/or a public phone system).

Output system 302 may include (if located outside of mask 100) and/or communicate with (e.g., if located in mask 100) any one of, some of, any combination of, or all of a monitor system, a handheld display system, a printer system, a speaker system, a connection or interface system to a sound system, an interface system to peripheral devices and/or a connection and/or interface system to a computer system, intranet, and/or internet, for example. Output system 302 may include a light source for producing flashes of light that are delivered to the user.

Input system 304 may include (if located outside or mask 100) and/or communicate with (e.g., if located in mask 100) any one of, some of, any combination of, or all of a keyboard system, a mouse system, a track ball system, a track pad system, buttons on a handheld system, a scanner system, a microphone system, a connection to a sound system, and/or a connection and/or interface system to a computer system, intranet, and/or internet (e.g., IrDA, USB), for example.

Memory system 306 may include, for example, any one of, some of, any combination of, or all of a long-term storage system, such as a hard drive; a short-term storage system, such as random access memory; a removable storage system, such as a floppy drive or a removable drive; and/or flash memory. Memory system 306 may include one or more machine-readable mediums that may store a variety of different types of information. The term machine-readable medium is used to refer to any medium capable carrying information that is readable by a machine. One example of a machine-readable medium is a computer-readable medium. Another example of a machine-readable medium is paper having holes that are detected that trigger different mechanical, electrical, and/or logic responses. The term machine-readable medium also includes mediums that carry information while the information that is in transit from one location to another, such as copper wire and/or optical fiber. In an embodiment, memory system 306 may include a device in the cloud to store data and/or process computation. Memory system 306 may store machine instructions for implementing the application, via which the user enters information related to their sleep schedule and interacts with the hardware in the mask or glasses or other circadian rhythm therapy device.

Processor system 308 may include any one, some, a combination, or all of multiple parallel processors, a single processor, a system of processors having one or more central processors and/or one or more specialized processors dedicated to specific tasks. Also, processor system 308 may include one or more Digital Signal Processors (DSPs) in addition to or in place of one or more Central Processing Units (CPUs) and/or may have one or more digital signal processing programs that run on one or more CPU.

Baseband processor system 312 is optional and baseband processor system 312 controls functions related to the telephony. For example, baseband processor system 312 processes incoming phone signals converting the signals into voice messages and/or ring tones and converting user entered key pad sequences into signals representing the dialing a phone number and user entered voice/audio messages, via a microphone, as part of a phone conversation. Since telephone conversations and telephone messaging works better when processed in a fast speed, the baseband processor system is a processor system that is dedicated to the telephone functions. Baseband processor system 312 may function independently of processor system 308 and/or may have a master slave relationship with processor system 308, in which baseband processor system 312 is subservient to processor system 308. In an embodiment, baseband processor system 312 is subservient to processor system 308 for some functions, whereas processor system 308 is subservient to baseband processor system 312 for other functions.

Input/output system 314 may include devices that have the dual function as input and output devices. For example, input/output system 314 may include one or more touch sensitive screens, which display an image and therefore are an output device and accept input when the screens are pressed by a finger or stylus, for example. The touch sensitive screens may be sensitive to heat and/or pressure. One or more of the input/output devices may be sensitive to a voltage or current produced by a stylus, for example. Input/output system 314 is optional, and may be used in addition to or in place of output system 302 and/or input device 304.

Processor system 308 and baseband processor system 312 are communicatively linked to one another and to output system 302, input system 304, memory system 306, and/or input/output system 314. In formation may be passed, via processor system 308, from any of output system 302, input system 304, memory system 306, and/or input/output system 314 to another of output system 302, input system 304, memory system 306, and/or input/output system 314. Processor system 308 and baseband processor system 312 are may be linked to output system 302, input system 304, memory system 306, and/or input/output system 314 by any one of, some of, any combination of, or all of electrical cables, fiber optic cables, and/or means of sending signals through air or water (e.g. wireless communications), or the like. Some examples of means of sending signals through air and/or water include systems for transmitting electromagnetic waves such as infrared and/or radio waves and/or systems for sending sound waves. In other embodiments, information may be shared between output system 302, input system 304, memory system 306, and/or input/output system 314 without participation of the processor system.

FIGS. 4-6 show the strap of that holds the mask on while being worn. Optionally, the strap includes elastic bands (or another type of band) that are attach pads to the left and right side of the sleep mask. The pads have a hook and loop material, so as to easily attach to one another and easily separate from one another. At one end of each pad may be a loop through which the bands are threaded to hold the pads, via the bands to the sleep mask. Optionally, each loops may be formed by folding over one end of the pad and attaching the edge of the folded portion to the body of the bad. Optionally, the edge may be sewn to body of the pad.

FIG. 7 shows a user wearing an embodiment of the mask. FIG. 7 shows the strap placement while the mask is being worn. The base of the user's ear, the part of the each ear that is connected to the user's head is sandwiched between an upper strap and a lower strap. In FIG. 7, the upper strap crosses above the ear and the bottom strap crosses below the strap.

FIG. 8 shows the eye mask with the charging port hole and the light pipe holes when the electronic insert is not currently installed. FIG. 9 shows the electronic pockets, the light pipes, and the eye sockets when the electronic insert is placed inside the mask.

FIGS. 10-12 show one embodiment of the electronic insert with light pipes and the charging port.

Alternatives and Extensions

Each embodiment disclosed herein may be used or otherwise combined with any of the other embodiments disclosed. Any element of any embodiment may be used in any embodiment.

Although the invention has been described with reference to specific embodiments, it will be understood by those skilled in the art that various changes may be made and equivalents may be substituted for elements thereof without departing from the true spirit and scope of the invention. In addition, modifications may be made without departing from the essential teachings of the invention.

The invention claimed is:

1. A system comprising:
a sleep mask;
the sleep mask including at least:
a housing including one or more sites for installing electronic components,
at least two holes for mounting light pipes for shining light on eyes of a user,
a light pipe system including one or more light pipes held in at least the two holes, a first of the two holes being positioned so that when a light is activated, the light pipe system illuminates a first of two user eyes via a first of the two holes and a second of the two holes being positioned so that the light pipe system illuminates a second of the two user eyes via a second of the two user holes;
electronics installed at the one or more sites, the electronics including a controller that controls a light source that is in communication with the light pipe system to produce of pattern of light on a side of the sleep mask that faces the user while the sleep mask is being worn; and
an adjustable strap that is adjustable to different head sizes, ear sizes, and user positions, wherein:
the light pipes include a first translucent structure and a second translucent structure;
the first and second translucent structures protrude from an inner side of the housing towards the eyes of the user;
each of the first and second translucent structures include an enlarged part at an end of the respective translucent structure, the each of the first and second translucent structures extending through a respective hole of the two holes, the enlarged parts being sized to anchor the light pipes in the two holes so as to hold the electronics, the light pipe system, and the sleep mask together.

2. The system of claim 1, wherein the sleep mask further includes two eye covers that cover the eyes of the user when the sleep mask is being worn, and the housing includes a pocket configured to hold the electronics, the pocket being located between the two eye covers.

3. The system of claim 2, wherein the pocket has an opening, and the opening is configured to allow the electronics to be removed and reinstalled, and the pocket is configured to hold the electronics in a desired position, by registering protruding parts of the electronics in pre-formed holes in the sleep mask.

4. The system of claim 2, wherein the pocket is configured to hold the electronics permanently inside the sleep mask.

5. The system of claim 2, wherein the pocket is located at least partially at a location that covers a top portion of a bridge of a nose of the user when the sleep mask is worn on the user.

6. The system of claim 2, wherein the pocket is located above a location that covers a bridge of a nose of the user when the sleep mask is worn on the user.

7. The system of claim 2, wherein the pocket is located closer to a top of a portion of the sleep mask between two eye portions than a bottom of the portion between the two eye portions.

8. The system of claim 2, wherein the adjustable strap includes at least two straps;
the at least two straps form at least two loops,
the at least two loops includes a left loop, and the left loop is attached to a left end of the sleep mask,
the at least two loops includes a right loop, and the right loop is attached to a right end of the sleep mask,
the sleep mask having a top and a bottom,
the top being a portion of the sleep mask that is furthest from a ground when the sleep mask is worn by the user, and
the bottom being a portion of the sleep mask that is closest from the ground when the sleep mask is worn by the user,
a portion of the sleep mask that attaches the two eye covers is above a nose of the user, and above portions of the two eye covers, the two eye covers extend below a bottom of the portion bridging the eye covers.

9. The system of claim 8,
wherein at least an upper portion of the right loop is attached to a top of the right end of the sleep mask and at least a lower portion of the right loop is attached to a bottom of the right end of the sleep mask;
wherein at least an upper portion of the left loop is attached to a top of the left end of the sleep mask and at least a lower portion of the left loop is attached to a bottom of the left end of the sleep mask;
the top being an edge that is above the two eye covers and the bottom being a portion that is below the two eye covers.

10. The system of claim 8,
wherein the left loop has a left loop fastener and the right loop has a right loop fastener;
the left loop fastener is configured to be detachably fastened to the right loop fastener.

11. The system of claim 10,
wherein the right loop fastener includes a right pad attached to the right loop;
the left loop fastener includes a left pad attached to the left loop, and the left loop fastener is configured to be adjustably connected to the right pad of the right loop fastener.

12. The system of claim 11,
wherein the right pad has a hook and loop material, and the left pad has a hook and loop material that connects to the hook and loop material on the right pad.

13. The system of claim 8,
wherein the left loop is configured to be wide enough so that an average person's ear fits in within the left loop with an upper portion of the left loop above a portion of a left ear and a lower portion of the left loop below a portion of the left ear;
the right loop is configured to be wide enough so that the average person's ear fits in within the right loop with an upper portion of the right loop above a portion of a right ear and a lower portion of the right loop below a portion of the right ear.

14. The system of claim 1, wherein the sleep mask has two eye portions, the two eye portions are configured to cover the eyes of the user, the at least two holes for the light pipes are located in the two eye portions, and each of the two eye portions have at least one hole for at least one light pipe.

15. The system of claim 14, wherein each eye portion of the two eye portions includes a cupped region where the at least one hole for at least one light pipe are located in the cupped region.

16. The system of claim 1, wherein a distance between a center of each of the at least two holes for the light pipes are within a range of 30-150 mm.

17. The system of claim 1, wherein when the sleep mask is worn, the sleep mask includes the light pipes, and an end of the light pipes that face the user are located at a position within a distance of 5-25 mm away from a surface of the eyes of the user.

18. The system of claim 1, wherein the sleep mask includes the light pipes, and when the sleep mask is worn, an angle in which a center of a respective light pipe pointing to is between 0 and 72 when the light pipes are located closer to a nose than ears of the user and between 0 and 86 degrees when the light pipes are located closer to the ears than the nose, from a perpendicular line emanating from pupil openings of the eyes of the user, while the user is looking straight ahead, a direction parallel to the line is 0 degrees.

19. The system of claim 1, further comprising
one or more or more lights that are positioned to be in optical communication with the light pipes.

20. The system of claim 1, wherein the adjustable strap includes straps attached to the sleep mask for holding the sleep mask on the face of the user, the straps being configured for being adjusted according to a user's preference.

21. The system of claim 1, wherein each of the light pipes includes a diffuser, a scattering material, and/or a diverging lens to spread light evenly across the user's eyes, and each of the light pipes are flexible or adjustable to adapt to different facial structures.

* * * * *